United States Patent [19]

Ruelle et al.

[11] Patent Number: 4,680,958
[45] Date of Patent: Jul. 21, 1987

[54] APPARATUS FOR FAST DETERMINATION OF THE RHEOLOGICAL PROPERTIES OF THERMOPLASTICS

[75] Inventors: Jean-Jacques Ruelle, Saint-Remy Geest; Giacomo d'Andrea, Brussels; Léopold Asselberghs, Merchtem, all of Belgium

[73] Assignee: Solvay & Cie, Brussels, Belgium

[21] Appl. No.: 886,439

[22] Filed: Jul. 17, 1986

[30] Foreign Application Priority Data

Jul. 18, 1985 [FR] France .................... 85 11146

[51] Int. Cl.⁴ ........................................... G01N 11/08
[52] U.S. Cl. ............................................................. 73/56
[58] Field of Search ................................................ 73/56

[56] References Cited

U.S. PATENT DOCUMENTS

| | | | |
|---|---|---|---|
| T869,014 | 7/1969 | Gray, Jr. et al. | 73/56 |
| 2,780,096 | 2/1957 | Noble et al. | 73/56 X |
| 3,270,553 | 7/1964 | Ballman et al. | 73/56 |
| 3,526,126 | 9/1968 | Wilchinsky et al. | 73/56 |
| 4,229,970 | 10/1980 | Barker et al. | 73/56 |
| 4,333,336 | 5/1980 | Myerholtz et al. | 73/56 |
| 4,425,790 | 12/1981 | Bice et al. | 73/55 |
| 4,449,395 | 4/1982 | Kurtz et al. | 73/56 |

FOREIGN PATENT DOCUMENTS 21542 2/1983 Japan .......................... 73/56

Primary Examiner—Stewart J. Levy
Assistant Examiner—Joseph W. Roskos
Attorney, Agent, or Firm—Spencer & Frank

[57] ABSTRACT

Apparatus composed of a control and monitoring unit 1, a thermostated cylinder 2 receiving a measured quantity of material to be evaluated, a plunger 3 sliding in the cylinder 2, an exchanger system enabling the cylinder 2 to be equipped with a suitable die 6 for the measurement to be carried out, a stepping-control motor 7 ensuring a monitored travel of the plunger 3, a force-sensor 9 yielding a signal as a function of the force applied to the plunger 3, and an electronic microprocessor system monitoring the stepping motor 7 as a function of the position of the piston and/or of the signal emitted by the force-sensor 9 at the end of the time assigned to the thermal conditioning of the measured quantity to be evaluated, the plunger 3 is situated at a distance from the die 6 permitting the measurement and acts for 10 to 180 seconds on the measured quantity according to a parameter of the speed of travel of the plunger or of the applied force specified by the measurement to be carried out.

12 Claims, 3 Drawing Figures

APPARATUS FOR FAST DETERMINATION OF THE RHEOLOGICAL PROPERTIES OF THERMOPLASTICS

The present invention relates to an apparatus for fast and accurate determination of rheological properties of thermoplastics, such as melt index, viscometric curves and/or extrusion swelling.

In the processes for manufacturing and converting thermoplastics, it is important to have prompt access to as much informations as possible on the rheological properties of these materials, so that these operations can be controlled efficaciously.

To be sure, devices which enable certain rheological properties of thermoplastics to be evaluated rapidly and even continuously are already known. However, these devices are specific for evaluating an individual property, and they cannot operate in accordance with the usual standards.

Thus, the Porpoise Viscosimeter, developed by GEC Electrical Projects Marine and Offshore, which comprises a gear pump in relation with a capillary undoubtedly permits a continuous evaluation of the viscosity of a thermoplastic, but this device cannot be readily adapted to the measurement of another rheological property such as, for example, a melt index.

The aim of the present invention is to overcome these disadvantages and to provide a universal apparatus which makes it possible to evaluate various rheological properties such as melt indices, viscosities and/or extrusion swellings, and to do this according to the standards which apply, and in a minimum time or according to a faster but entirely wholly accurate method.

Consequently, the present invention relates to an apparatus for fast determination of the rheological properties of a thermoplastic, comprising:

a control and monitoring unit;

a cylinder intended to receive a determined measured quantity of the thermoplastic to be evaluated, and equipped with a thermostated jacketing for thermal conditioning, for a period of at least 300 seconds and at a predetermined temperature, of the measured quantity of the thermoplastic to be evaluated;

a plunger which can slide in the cylinder so that it is applied to the measured quantity of the thermoplastic;

an exchanger system enabling the cylinder to be fitted with a capillary die which is adapted to the rheological measurement to be carried out;

a stepping-control motor ensuring a monitored travel of the plunger in the cylinder to expel the thermoplastic through the capillary die, and a force-sensor arranged between the motor and the plunger, giving a signal which is a function of the force applied to the plunger, characterized in that it additionally comprises an electronic microprocessor system monitoring the stepping motor as a function of the position of the plunger and/or of the signal emitted by the force-sensor, so that, at the end of the thermal conditioning, the plunger is situated at a distance from the capillary die which permits the measurement to be carried out and acts, for a period of time ranging from 10 to 180 seconds, on the measured quantity of thermoplastic to be evaluated, according to a parameter of the speed of travel or of the applied force which is required by the type of rheological measurement to be carried out.

The apparatus according to the invention can consequently be used either for determining a melt index or a viscosity of a thermoplastic, simply by being equipped with a suitable capillary die and by changing the electronic microprocessor system either to control the force applied to the plunger or to control the rate of travel of the plunger.

In addition, according to an alternative embodiment which turns out to be especially advantageous, the apparatus according to the invention can be equipped with a device enabling the lace of thermoplastic extruded to be cut off flush with the capillary die and with a device for detecting the leading end of the new extruded lace situated at a predetermined distance from the end of the capillary die. As a result of this, the apparatus according to the invention can also be used to determine, in a known manner, the extrusion swelling characteristics of a thermoplastic, this measurement being generally carried out jointly with viscosity measurements.

According to a preferred embodiment, the device for cutting off the extruded lace consists of a flexiblebs blade fixed at the end of a rotary shaft which can be actuated automatically by an electric motor, and the detection device consists of optical fibres arranged in a ring which is concentric with the axis of the cylinder, the distance between the optical detection device and the end of the capillary die being generally fixed at 70 mm. It is quite obvious, however, that these cut-off and detection devices are not critical in any way and that, consequently, other reliable devices can be envisaged.

The control and monitoring unit contains the electronic microprocessor system which monitors the stepping motor, the temperature regulator and the electronic hardware required for managing the use sequences, for measurements, for calculations and for displaying results, and so on. The front face of this unit comprises the control and selection buttons, the display tables and, if appropriate, alarm tell-tales intended to signal any defective operation. The control unit can be connected to a printer and/or to a screen which display the test conditions and the results obtained.

According to an advantageous embodiment, the cylinder, the thermostated jacketing and the plunger of the apparatus according to the invention are produced in accordance with the ASTM standard D 1238-82 so as to permit standardized measurements insofar as the determination of the melt indices is concerned.

To the same end, the die-changer device, which can be of the slide or turret type is preferably designed to be fitted with a set of standardized dies, i.e. with an L/D: 8/2.095 die for measuring the melt index, and with L/D: 15/1 and 30/2 dies for measuring viscosity and/or swelling. Preferably, the die-changer device is equipped with proximity detectors ensuring a monitoring of the correct choice of the die as a function of the rheological property to be determined and monitoring the correct location of this die on the cylinder. These detectors can activate alarm tell-tales provided on the control and monitoring unit.

As has been stated, the travel of the plunger in the cylinder is ensured by a stepping-control motor whose control impulses are monitored by the electronic microprocessor system. The driving of the plunger by this motor is, preferably, ensured by a screw-and-nut system. According to a preferred embodiment, the transmission system and the motor are chosen so that a $1.10^{-3}$ m linear travel of the piston requires from 500 to 10,000 and preferably from 1000 to 3000 motor control impulses. In this manner, the position of the plunger can be determined at any time with an accuracy of the order of $0.5.10^{-6}$ m.

The force-sensor, arranged between the stepping control motor and the plunger is, preferably, equipped with measuring elements consisting of strain-gauge force cells.

Given that the rheological measurements which can be carried out by means of the apparatus according to the invention can require the application of forces to the plunger which can vary from a few newtons to several thousand newtons, both during the measurements and during the thermal conditioning, it is not possible to use single force cell to ensure a continuous and accurate measurement of these forces in all cases of use. In practice, therefore, use is made of a plurality of force cells having gradually increasing measurement ranges.

Thus, for example, a force cell with a range of 0–100 N and a force cell with a range of 0–2000 N can be advantageously used, these two cells being fixed to a pivoting cantilever beam enabling either cell to be used alternately, depending on the rheological measurement to be carried out and depending on the thermoplastic to be evaluated.

In this case, it may be advantageous to provide the cantilever beam with a third position, in which position both force cells are out of service and at a distance from the axis of the cylinder, so as to permit easy access to the cylinder, for example for a cleaning operation.

According to a preferred embodiment, the forcesensor consists of a plurality of force cells arranged in series and with an increasing measurement range, each force cell being inserted in a casing which ensures that the force exerted on the force cell which it contains is transferred to the next cell having a higher measurement range when this force exceeds the maximum permissible value for this force cell.

For this purpose and according to a particularly valued embodiment, each successive force cell is inserted in a strong open casing, the various casings being superposed. The sizing of each casing is implemented so that the side wall of a casing comes into contact with the closed bottom of the preceding or following casing as soon as the value of the force transmitted to the force cell inserted in this casing reaches the maximum permissible value for this force cell, with the force cell inserted in the preceding or following casing, with a higher measurement range, ensuring thereupon that the force to be measured is picked up.

According to an embodiment which is preferred in this case, each force cell is, in addition, protected mechanically by a system for transmitting the force to be measured, consisting of a calibrated spring, prestressed to the maximum permissible value for each force cell, which ensures the transmission of the force to be measured. In this manner, when the force applied to any one force cell runs the risk of exceeding the maximum permissible value, the deformation of the corresponding calibrated spring prevents the application of an excessive force to the force cell.

In particular, any accident which could result from an excessive force accidentally transmitted to the force-measuring system is avoided by using a force-sensor equipped with force cells in series, which has just been described.

In addition, as will be explained later, the use of such a force-sensor makes it possible to carry out rheological measurements on widely different thermoplastics while still using an identical measured quantity of the thermoplastic to be evaluated.

In accordance with the invention, the apparatus additionally comprises an electronic microprocessor system which continuously monitors the stepping-control motor and, consequently, the travel of the plunger and/or the force applied to the latter, and which does this as a function of the position occupied by the plunger at any time and/or as a function of the signal emitted by the force-sensor both during the thermal conditioning phase and during the rheological measurement of the thermoplastic to be evaluated, so that at the end of the heat conditioning the plunger is situated at a distance from the capillary die which permits the measurement to be carried out and acts over a period of time ranging from 10 to 180 seconds on the plastic to be evaluated according to the parameters of rate of travel or of applied force which are required by the type of rheological measurement to be carried out, these parameters being, moreover, kept constant during the entire period of the measurement.

In fact, during the measurement of a melt index, the plunger has to apply a predetermined constant force to the thermoplastic, because such a measurement consists in determining the weight of plastic which is expelled through a specified capillary die, in a specified time and under the application of a specified force, whereas during a measurement of viscosity or of swelling the plunger has to be driven at a constant and predetermined rate of travel during the entire measurement. It thus appears that the electronic microprocessor system needs to exercise either a control of force or a control of speed, depending on the rheological measurement to be carried out. In addition, in order to obtain reproducible results, it is known that the rheological measurements must always commence when the plunger reaches a predetermined distance from the capillary die, this distance being generally fixed at 50 mm.

Force control—Measurement of melt indices

During the melt index measurement, the electronic system must ensure the control of the force applied to the plunger, the cylinder being in this case equipped with a die which is suitable for measuring a melt index.

During such a measurement, the electronic system, in a first step, after 5 to 30 seconds of thermal conditioning of the measured quantity of thermoplastic to be evaluated, monitors the stepping-control motor so that, for 50 to 150 seconds, the plunger applies to the measured quantity of plastic a constant force which is equal to that which should be applied during the measurement to be carried out, evaluates the rate of travel of the plunger under the effect of this force and determines the ideal control parameters as a function of the thermoplastic examined; in a second step, it monitors the stepping-control motor so that the force applied to the plunger is reduced or increased for a certain period of time and, in a third step, after 120 to 290 seconds of heat conditioning it monitors the steppingcontrol motor so that the plunger again applies to the measured quantity of thermoplastic to be evaluated a force equal to the force which should be applied during the measurement, the third step being initiated at a time such that the application of this force brings the plunger to the predetermined distance from the die permitting the measurement at the end of the time period assigned for the thermal conditioning, this force being kept constant during the entire duration of the subsequent measurement.

The apparatus according to the invention is consequently distinguished from the apparatuses of the prior art in that the set condition to be observed during the rheological measurement to be carried out, the constancy of the force applied by the plunger in the present case, is obeyed already before the measurement, so that, at the end of the thermal conditioning, the plunger is not only situated at the distance from the die which permits the measurement to be carried out, but has also been subject for sometime to the set conditions specified for the measurement.

In this manner, when the apparatus is used in its measurement phase, it is in a stable flow regime from the very beginning of the measurement.

In addition, like all the known apparatuses, the apparatus according to the invention makes it possible to perform the required rheological measurement at the end of the period of time specified for the thermal conditioning of the thermoplastic to be evaluated.

According to an alternative embodiment, which is preferred when no previous indication of the rheological characteristics of the thermoplastic to be evaluated is available, after 5 to 30 seconds of thermal conditioning, during the beginning of the first step the electronic system first monitors the stepping-control motor so that the plunger first applies to the measured quantity of thermoplastic a force which is appreciably lower than the force which needs to be applied during the measurement, and does this for 10 to 90 seconds, so as to permit a first evaluation of the gain of the electronic system and hence an estimate of the ideal duration of the next phase of the first step, during which the electronic system applies to the measured quantity of thermoplastic via the stepping-control motor, a force equal to that which needs to be applied during the rheological measurement to be carried out.

It has been found, in fact, that the operating parameters of the electronic system are substantially a function of the nature of the thermoplastic to be evaluated and show little dependence on the force applied to determine these parameters. As a result of this, the knowledge of the gain of the electronic system for a given applied force enables the gain to be calculated for a different applied force to a good approximation.

In other words, the knowledge of the rate of travel of the plunger under the effect of a weak force (1 to 20 N) makes it possible to evaluate the rate of travel of the plunger under a higher force to be applied during the measurement and, consequently, to determine a period for which this force is applied during the first step, which is compatible with bringing the plunger to the predetermined distance from the die at the end of the thermal conditioning.

During this first step, the apparatus carries out a new evaluation of the actual rate of travel of the plunger when the latter is subject to the force to be applied during the measurement.

Depending on the thermoplastic to be evaluated, this rate of travel of the plunger is either too high (fluid thermoplastic) or too low (viscous thermoplastic) to bring the plunger to the predetermined distance from the die at the end of the period assigned to the thermal conditioning.

In the first case, during the second step, the electronic system monitors the stepping-control motor so as to reduce the force applied to the plunger during a period of time such that after this time has elapsed the electronic system can again apply to the plunger, via the stepping-control motor, during the third step, the force to be used for the rheological measurement to be carried out, and thus bring this plunger to the predetermined distance from the die at the end of the time assigned to the thermal conditioning. According to a preferred embodiment, during the second step, the force applied to the plunger is reduced to zero, the stepping-control motor being no longer energized, this being done in order to reduce the duration of the second step to the minimum and hence to lengthen that of the third step.

In the second case, during the second step, the electronic system monitors the stepping-control motor so as to increase the force applied to the plunger during a period of time such that after this time has elapsed the electronic system can again apply to the plunger, via the stepping-control motor, during the third step, the force to be used for the rheological measurement to be carried out and bring the plunger to the predetermined distance from the die at the end of the time assigned for the thermal conditioning. According to a preferred embodiment, the force applied to the plunger during the second step is the maximum force which can be sustained by the apparatus, this again being done in order to shorten the duration of the second step and consequently to lengthen that of the third step.

Using the apparatus according to the invention, it is therefore possible to carry out measurements of melt indices as soon as the thermal conditioning is finished and to do this under excellent conditions, because the set condition to be observed during the measurement,—a constant force applied to the plunger—is obeyed already before the measurement begins and because the apparatus is thus already under proper conditions.

The melt indices are determined from the rate of travel of the plunger which is subject to the specified constant force.

The determination of melt indices under the usual loads of 3.19 N (0.325 kgf), 21.18 N (2.16 kgf), 49.03 N (5 kgf) or 211.8 N (21.6 kgf) can, in addition, be carried out in accordance with the ASTM Standard D 1238-82 Method A, that is to say with a measurement time ranging from 330 to 660 seconds, depending on the fluidity of the thermoplastic to be evaluated when hot, when an apparatus comprising an assembly—cylinder, plunger, die—conforming to this standard is employed, as is preferable.

However, in view of the fact that the use of a stepping-control motor enables the successive positions of the plunger to be determined with high accuracy and that the electronic system makes it possible to start the measurements under ideal conditions, it has been found that melt indices determined over a much shorter measurement time period, of the order of 10 to 60 seconds, and even less, are perfectly comparable with those obtained according to the method specified by the abovementioned standard, and that this is characterized by a remarkable reproducibility.

In practice, using the apparatus according to the invention, the Applicant Company usually takes 30 seconds to determine melt indices which are in perfect correlation with those determined according to the abovementioned ASTM standard.

The apparatus according to the invention is consequently found to be especially advantageous for carrying out fast routine monitoring measurements in a plant for the production or the conversion of thermoplastics and especially of polyolefins.

According to an embodiment of use of the apparatus according to the invention which is found to be advantageous, the apparatus is regulated so that it carries out at least three successive measurements of equal duration during the time assigned to the measurement and carries out a comparison between these measurements and their average so as to detect a possible high descrepancy (greater than 25%) making the determination suspect.

When the apparatus according to the invention is equipped with a force-sensor equipped with force cells in series, as is preferred, the force applied to the plunger during the thermal conditioning during the second step can vary within very wide limits and, as a result, the measured quantity of thermoplastic to be introduced into the cylinder during a measurement can be constant whatever the melt index of this material.

This characteristic feature of the apparatus according to the invention is found to be highly advantageous in the case where the intention is to make the operation automatic in order to carry out series of successive measurements on thermoplastics, for example by way of regular monitoring in a production plant.

Speed control—Viscosity and swelling measurement

The electronic microprocessor system is responsible, in this case, for controlling the rate of travel of the plunger, when this cylinder is equipped with a suitable die for the measurement to be carried out.

During such a measurement, after 5 to 30 seconds of thermal conditioning of the measured quantity of thermoplastic to be evaluated, the electronic system determines, as a function of the position of the plunger in contact with the measured quantity and of the assigned conditioning time, the mean speed at which the plunger must be made to travel to be brought to the predetermined distance from the die at the end of the time assigned for thermal conditioning, and it compares this mean speed with the constant speed to be given to the plunger for the measurement to be carried out, and then, in a first step, as a function of the result of this comparison, the electronic system monitors the stepping-control motor so that the plunger travels at a speed which is lower or higher than this speed and, in a second step, monitors the stepping-control motor so that the plunger travels at the constant speed required for the measurement which is to be carried out, this second step being initiated at an instant such that this constant speed of travel of the plunger brings the latter to the predetermined distance from the die at the end of the time assigned for the thermal conditioning, this constant speed of travel of the plunger being maintained during the entire duration of the measurement to be carried out.

In the second step, the electronic system sets a speed of travel which is lower than the mean speed when the constant speed of travel to be imposed on the plunger for the measurement to be carried out is higher than this mean speed and, conversely, makes the plunger travel at speed which is higher than the average speed in the opposite case.

In order to shorten the duration of the first step and consequently to lengthen that of the second step, it is preferable to make the plunger travel at a speed which is as low or as high as possible during the first step. In practice, the preferred choice is either a speed of travel which is zero, as a result of the stepping-control motor being stopped, or a speed of travel which is the fastest possible compatible with the mechanical strength of the apparatus.

The apparatus according to the invention is thus distinguished, yet again, from the apparatuses which are already known in that the set condition which is to be obeyed during the measurement to be carried out, a constant and predetermined speed of travel of the plunger in the present case, is maintained already before the measurement, with the result that when, at the end of the thermal conditioning, the plunger is situated at the distance from the die which permits the measurement to be carried out, it has already been moving for some time at the speed specified for the measurement to be carried out. When used during its measurement phase, the apparatus is thus again in a stable flow regime from the very beginning of the measurement to be carried out. The viscosity measurement is calculated from the force applied to the plunger to maintain the set speed.

According to a preferred embodiment of the apparatus, during the 30 seconds preceding the instant when the plunger reaches the predetermined distance from the die, the apparatus executes a plurality of successive measurements of the force applied to the plunger by means of the force-sensor, and compares these measurements with each other and with their mean in order to detect any major discrepancy, for example in excess of 5%, indicating a possible flow irregularity, that is to say an oscillating flow which can vitiate the measurement to be carried out. In the latter case, the measurement sequence is stopped, and an alarm tell-tale provided on the front panel of the apparatus control unit can inform the operator of the reason for this stoppage.

Thus, the apparatus according to the invention permits the dynamic viscosity of any plastic to be determined, at any rate gradient, the measurement being capable of being carried out in 30 seconds or in a shorter time, and with remarkable accuracy.

To carry out a simultaneous additional measurement of extrusion swelling, the lace extruded through the die is cut off flush with the latter as soon as the plunger reaches the predetermined distance from the die and the detector is brought into action. As soon as the leading end of the extruded lace reaches the detector, the apparatus can calculate the swelling and display it on the front panel of the control unit. This swelling is determined from the space traversed by the plunger at the time when the new lace is detected.

The electronic microprocessor system can be produced in any way, provided that it ensures the controls described above.

In general, this system comprises:

a microprocessor system which programs and manages the various measurement sequences;

a stepping motor control unit which, under the monitoring by the microprocessor, receives an analogue control voltage originating either from a force-regulator, in the case of a melt index measurement, or from a set value generator, in the case of a measurement of viscosity and/or swelling, and whose output supplies the motor with the control pulses required for its operation, and a force-regulator, brought into action only when a melt index is measured, which is of the proportionalintegral type and which uses the gain values chosen automatically under the monitoring of the electronic microprocessor system.

Furthermore, the apparatus according to the invention is described in greater detail by the example of practical embodiment which is given below and in the description of which reference will be made to the attached figures, in which.

Figure 1:
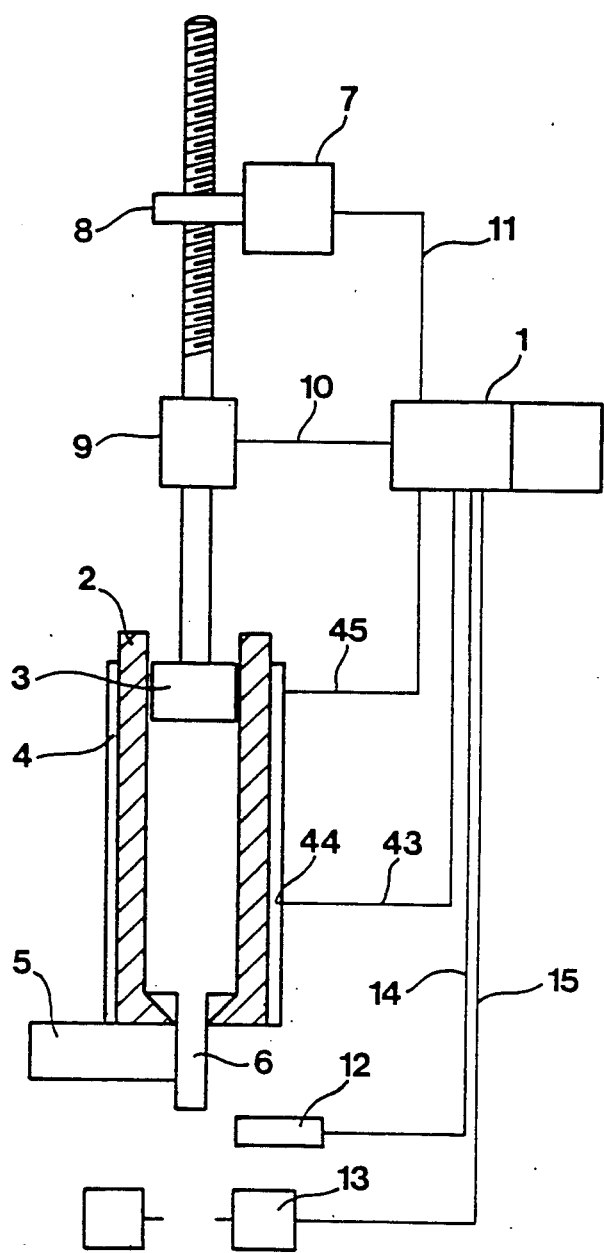
FIG. 1 is a diagram of the apparatus according to the invention.

As can be seen in the diagram of FIG. 1, the apparatus according to the invention comprises a control and monitoring unit 1 containing, in particular, the electronic microprocessor system, a cylinder 2 and a plunger 3, which are constructed in accordance with the ASTM Standard D 1238-82, the cylinder 2 being fitted with a thermostated jacket 4, also constructed in accordance with the abovementioned standard.

The cylinder 2 is additionally provided with a slide-type changing device 5 which enables this cylinder to be equipped with a suitable die 6 for the rheological measurement to be carried out.

The travel of the plunger 3 in the cylinder 2 is provided by a stepping-control motor 7, through the intermediacy of the screw-and-nut system 8.

A force-sensor device 9, which will be described in detail later, is arranged between the motor 7 and the plunger 3 and transmits, via the cable 10, a signal which is proportional to the force exerted by the plunger, to the control unit 1. The motor 7 is controlled by the cable 11 connected to the control unit 1.

The apparatus also comprises a device 12 for sectioning the lace flush with the die 6, the working part of which consists of a flexible blade fixed at the end of a rotary shaft driven by an electric motor, and an optical device 13 for detecting the lace and situated 70 mm from the end of the die, and consisting of optical fibres arranged in a ring which is concentric with the axis of the cylinder 2, these two devices being connected to the control unit 1 by cables 14 and 15.

Figure 2:
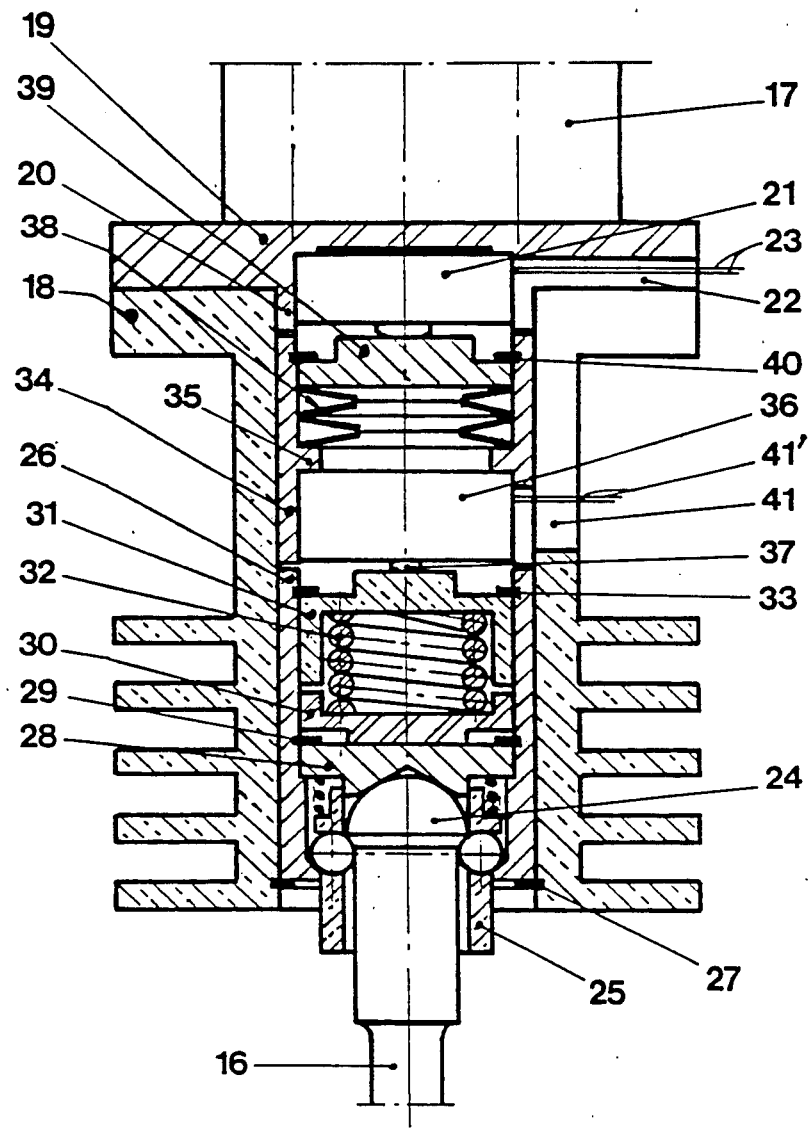
FIG. 2 is a sectional view of a force-sensor, equipped with two force cells in series.

As can be seen, especially in FIG. 2, the forcesensor 9 connected between the rod 16 for operating the piston 3 and the travel control 17 monitored by the stepping motor 7, consists of an annular cylindrical outer casing 18 containing the measurement devices and equipped in its upper part with a circular cover 19 connected directly to the travel control 17. The cover 19 has an annular internal rim 20 which fits into the outer casing 18 and which defines a cylindrical unit or cell-carrier, in which a strain-gauge force cell 21 with a measurement range of 0 to 2000 N is inserted, an aperture 22 being provided in the cover 19 and in the rim 19 to allow the passage of the cables 23 for connecting the force cell 21.

The head 24 of the plunger operating rod 16 is held by a ball race 25 in an annular plunger-carrier 26, of cylindrical appearance, which can travel in the outer casing 18 and which is held down in this outer casing by an annular spring 27. The head 24 of the plunger operating rod 16 also bears on a pusher 28 which itself bears on the plunger-carrier 26 and which can drive the plungercarrier 26 upwards by means of the annular spring 29 provided in this plunger-carrier.

The plunger-carrier 26 is also equipped with an assembly comprising a dish 30 and a pusher 31 which are held apart from each other by a calibrated spring 32 prestressed to a tension of 100 N, the dish 30 bearing on the pusher 28 and the pusher 31 being held against the action of the calibrated spring 32 by an annular spring 33 provided in the plunger-carrier 26.

The outer casing 18 also contains a cylindrical cell-carrier 34, annular in cross-section and provided with an inner rim 35, this cell-carrier 34 being situated above the plunger-carrier and separated slightly from the latter.

The lower part of the cell-carrier 34 forms a casing in which a force cell 36 with a measuring range of 0 to 100 N is inserted, bearing on the inner rim 35 and with its measuring pusher 37 in contact with the pusher 31. Apertures 41 are provided in the outer casing 18 and in the cell-carrier 34 to allow the passage of the connecting cables 41' of the force cell 36. The cables 23 and 41' form, in fact, the cable 10, which is connected to the control and monitoring unit.

The upper part of the cell-carrier 34, situated above the inner rim 35, is equipped with a calibrated spring 38, prestressed to a tension of 2000 N, which bears On the inner rim 35 and tends to push back a pusher 39 which is held in the cell-carrier 34 by an annular spring 40 provided in this cell-carrier.

In a rest position, the pusher 39 is in direct contact with the measuring pusher of the force cell 21 and the ends of the cell-carrier 34 are held away, with a predetermined clearance, from the ends of the plunger-carrier 26 and of the rim 20.

The operation of the device described in this manner is as follows: the device as illustrated being at rest, that is to say not subject to the action of a force to be measured.

Under the action of such a force, the plunger operating rod 16 tends to enter, with its head 24, the outer casing 18. This force is thus transmitted, via the pusher 28, the plunger-carrier 26 and the pusher 31, to the force cell 36 which, consequently, emits a signal proportional to this force.

As soon as the force to be measured exceeds 100 N, the spring 32 is compressed and the force transmitted to the force cell remains at a value of 100 N, preventing any damage to this cell.

Taking into account the fact that the clearance provided between the plunger-carrier 26 and the cell-carrier 34 is calculated so that these two components come into contact as soon as the force to be measured reaches 100 N, any exerted force which is greater than this value continues, thereafter, to be transmitted via the plungercarrier 26, the cell-carrier 34 and the pusher 39, to the force cell 21 which, in its turn, emits a signal proportional to this force.

Lastly, when the force exerted by the plunger operating rod 16 accidentally exceeds 2000 N, the spring 38 is compressed in its turn and the force transmitted to the force cell 21 remains at the maximum value of 2000 N. Taking into account the fact that the clearance between the cell-carrier 34 and the rim 20 is calculated so that these two components come into contact as soon as the force to be measured reaches 2000 N, a force exerted by the plunger and accidentally exceeding 2000 N would be taken up by the cover 19 without any risk of mechanical damage to the force cells 21 and 36.

Figure 3:
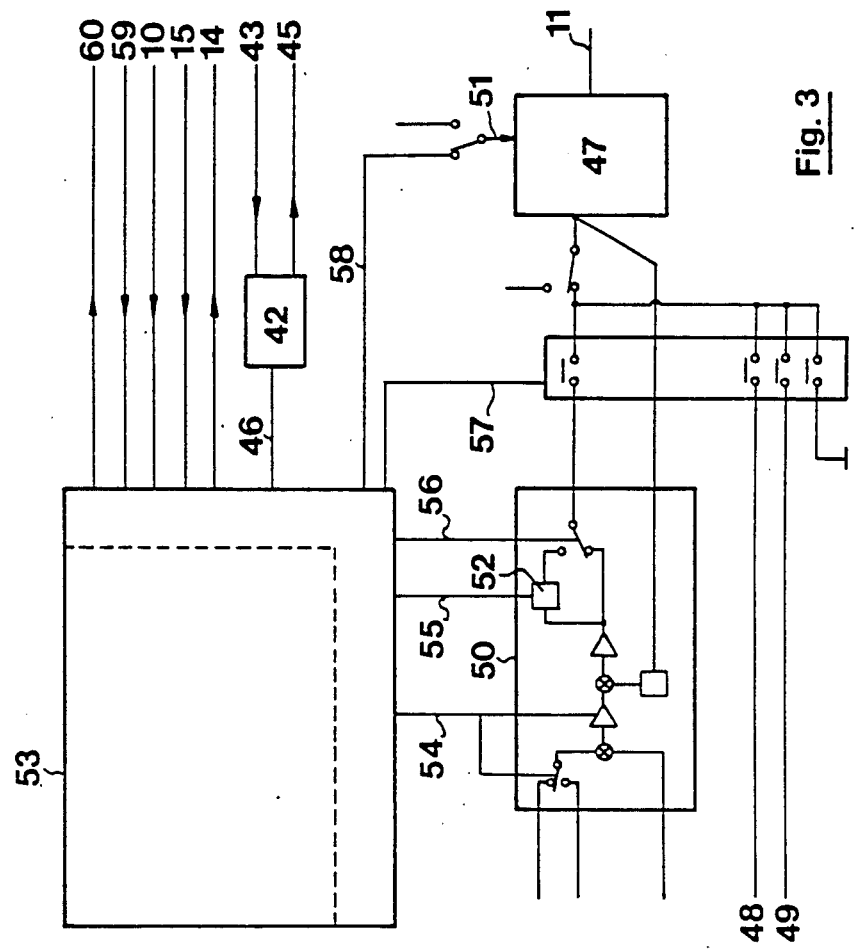
FIG. 3 is a diagram of the control and monitoring unit.

As can be seen from the diagram in FIG. 3, the control and monitoring unit 1, which contains the electronic system which manages the measurement, control, display and alarm functions, comprises a temperature regulator 42, a stepping motor control unit 47, a force regulator 50 and a microprocessor system 53.

The temperature regulator 42, of the PID type (proportional-integral-derivative) is connected by the cable 43 to a temperature probe 44 of the Pt 100 type, arranged in the jacketing 4 of the cylinder 3, and ensures the thermostating of the jacketing 4 by means of a heating element (not shown) powered via the cable 45. It is obvious that several probes could be arranged at intervals along the jacketing 4. In the event that a high or low temperature limit is exceeded, the temperature regulator 42 transmits an alarm signal to the microprocessor system 53 through the cable 46.

The stepping motor control unit 47 receives an analogue voltage (0–10 V) originating either from the force regulator 50 (in the case where a melt index is measured) or from a set value generator (not shown) via the cables 48 and 49, (in the case where a viscosity and/or a swelling are measured). In the latter case, the cables 48 and 49 deliver a voltage corresponding either to a maximum speed of travel of the plunger or to a set speed (speed specified by the measurement). An all-or-nothing input 51 determines the direction of operation of the stepping motor (ascent or descent of the plunger).

The output 11 from this unit supplies the power pulses required for controlling the stepping motor, the frequencies of these pulses being proportional to the input analogue voltage.

The image of the pulses which are actually transmitted to the stepping motor is input into the microprocessor system, where an accumulating counter (not shown) enables the instantaneous positions of the plunger driven by the stepping motor to be accurately determined.

The force regulator 50 comes into action only during melt index measurement. It is of the proportionalintegral type. Monitored by the microprocessor system 53, it enables gain values to be chosen automatically as a function of the specimen to be evaluated. A "sample and hold" circuit 52 is provided to meet the requirements of the measurement profile chosen (memorization of the voltage to be applied in the final step).

The microprocessor system 53 consists of two distinct parts:

on the one hand, the set of industrial microprocessor cards comprising the processor (8085 A type), the RAM and ROM memories, the pulse counters, the input and output interfaces and, if appropriate, an output to a printer and/or a screen, which are not shown.

The inputs and outputs comprise, in particular, the cables 54, 55, 56 and 57 for output to the force regulator 50, the cable 58 for output to the control unit 47, the input cable 46 for the temperature regulator alarm, the input cable 10 for the signal emitted by the force-sensor 9, the output cable 14 to the lace-cutting device 12, the input cable 15 of the lace detector 13, the input cables 59 of the fault detectors (faulty or incorrectly placed die, absence of material to be tested, etc) and the output cables 60 to the alarm or display tell-tales;

on the other hand, the set of adapting or interfacing cards forming the connection between the inputs and outputs to the other components. This interface adapts the voltage level or the shape of the all-or-nothing signals (position sensors) to the requirements of the microprocessor cards.

The program entered in the ROM memory of the microprocessor 53 comprises the measurement profile adopted, the inputs/outputs management, the management of the alarms and displays, and the optional output to a printer and/or a screen.

A large number of tests have been carried out using the apparatus as described, showing that the latter is highly accurate and perfectly reliable.

A selection from these tests is given below by way of illustrative examples.

EXAMPLE 1

The apparatus described has been used to evaluate the 2.16 melt index of an Eltex B4020 polyethylene manufactured by the Applicant Company.

The measurement was carried out in 30 seconds after thermal conditioning at 190° C. and produced a value of 2.078 g/10 min. A parallel test carried out in accordance with the ASTM Standard D 1238-82, by means of a conventional apparatus (CEAST 6542/000 melt indexer) gave a value of 2.05±0.06 g/10 min.

A third test, carried out with the apparatus described, but in which the measurement was carried out according to the conditions of the ASTM Standard D 1235-82 gave a value of 2.005 g/10 min.

EXAMPLE 2

The apparatus described was used to evaluate the 0.325 melt index of an Eltex A1050 polyethylene produced by the Applicant Company, the measurement being carried out according to the conditions of the ASTM Standard D 1238-82. The test gave a result of 0.681 g/10 min, corresponding in practice to the average melt index determined with the aid of conventional apparatuses.

EXAMPLE 3

The apparatus described, fitted with an L/D=15/1 die was used to evaluate the dynamic viscosity and the swelling, at a rate gradient of 100 s$^{-1}$ (42) of an Eltex A1050 polyethylene produced by the Applicant Company. The measurement, carried out in 30 seconds after the thermal conditioning at 190°, gave a value of 7385.23 dPa s for the viscosity and 1.339 for the swelling.

A parallel test carried out by means of a CIL (Canadian Ind. Ltd.) viscometer gave a viscosity value of 7480+250 dPa s.

EXAMPLE 4

The apparatus used in Example 3 was employed to evaluate the dynamic viscosity and the swelling, at a rate gradient of 1000 s$^{-1}$ (43) of an Eltex A3999 polyethylene produced by the Applicant Company. The measurement, carried out in 30 seconds after the thermal conditioning at 190°, gave a value of 410.01 dPa s for the viscosity and 1.481 for the swelling. It should be noted in this case that, in view of the extreme fluidity of this resin, it is impossible to measure its swelling by conventional methods.

A parallel test carried out by means of a CIL viscometer gave a viscosity value of 400+25 dPa s.

EXAMPLE 5

The apparatus described, fitted with an L/D:30/2 die, was used to evaluate the dynamic viscosity and the swelling, at a rate gradient of 100 s$^{-1}$ (42) of an Eltex B3002 polyethylene produced by the Applicant Company.

The measurement, carried out in 30 seconds after the thermal conditioning at 190° C., gave a value of 17538.5 dPa s for the viscosity and 1.539 for the swelling.

A parallel test carried out by means of a Gottfert HKV 2000 viscometer gave a viscosity value of 17500+350 dPa s.

It appears, as a result, that the apparatus according to the invention is perfectly suitable for evaluating the rheological properties of thermoplastics, either in accordance with the usual standards or in accordance with a faster method.

We claim:

1. Apparatus for the rapid determination of the rheological properties of a thermoplastic, comprising:
   a control and monitoring unit (1)
   a cylinder (2) intended to receive a determined measured quantity of the thermoplastic to be evaluated, and equipped with a thermostated jacketing (4) for the thermal conditioning, during at least 300 seconds and at a predetermined temperature, of the measured quantity of thermoplastic to be evaluated
   a plunger (3) capable of sliding in the cylinder (2) so as to be applied to the measured quantity of thermoplastic
   an exchanger system (5) enabling the cylinder to be equipped with a capillary die (6) suitable for the rheological measurement to be carried out a stepping-control motor (7) ensuring a monitored travel of the plunger (3) in the cylinder (2) to expel the thermoplastic through the capillary die (6), and
   a force-sensor (9) arranged between the motor (7) and the plunger (3), yielding a signal as a function of the force applied to the plunger (3), characterized in that said apparatus additionally comprises an electronic microprocessor system monitoring the stepping-control motor (7) so that at the end of the thermal conditioning the plunger (3) is situated at a distance from the capillary die (6) which permits the measurement to be carried out and acts over a period of time ranging from 10 to 180 seconds on the measured quantity of thermoplastic to be evaluated in accordance with a parameter of speed of travel or of applied force specified by the type of rheological measurement to be carried out.

2. Apparatus according to claim 1, characterized in that, in order to permit a rheological measurement of swelling, said apparatus is equipped with a device (12) permitting the lace of extruded thermoplastic to be cut off flush with the capillary die, and an optical device (13) for detecting the extruded lace situated at a predetermined distance from the end of the capillary die (6).

3. Apparatus according to claim 1, characterized in that the cylinder (2), the thermostated jacketing (4) and the plunger (3) are made according to the ASTM Standard D 1238-82.

4. Apparatus according to claim 1, characterized in that the force-sensor (9) consists of a plurality of strain-gauge force cells (21) (36), arranged in series, each force cell being inserted into a casing which ensures the transfer of the force exerted on the force cell which it contains to the following cell having a higher measurement range when this force exceeds the maximum permissible value for this measurement cell.

5. Apparatus according to claim 4, characterized in that each force cell (21) (36) is, additionally, protected mechanically by a system for transmitting the force to be measured, consisting of a calibrated spring (32) (38) prestressed to the maximum permissible value for each force cell.

6. Apparatus according to claim 1, equipped with a suitable die (6) for the measurement of a melt index, characterized in that said electronic microprocessor systems comprises means for monitoring which, in a first step, after 5 to 30 seconds of thermal conditioning of the measured quantity of the thermoplastic to be evaluated, monitors the stepping-control motor (7) so that during 50 to 150 seconds the plunger (3) applies to the measured quantity of thermoplastic a force equal to that which has to be applied for the measurement of a melt index, evaluates the speed of travel of the plunger (3) under the effect of this force and determines the ideal control parameters as a function of the thermoplastic examined, and, in a second step, monitors the stepping-control motor (7) so that the force applied to the plunger (3) may be reduced or increased for a period of time and, in a third step, after 120 to 290 seconds of thermal conditioning, monitors the stepping-control motor (7) so that the plunger (3) again applies to the measured quantity of thermoplastic to be evaluated a force equal to the force which has to be applied during the measurement, the third step being initiated at an instant such that the application of this force brings the plunger (3) to the predetermined distance from the die (6) permitting the measurement at the end of the time assigned for the thermal conditioning, this force being kept constant for the entire duration of the subsequent measurement.

7. Apparatus according to claim 6, characterized in that during the beginning of the first step the electronic system monitors the stepping-control motor (7) so that the plunger (3) first applies to the measured quantity of thermoplastic a force lower than the force which has to be applied during the measurement, this being done during 10 to 90 seconds so as to permit a first evaluation of the gain of the electronic system and an estimation of the ideal duration of the following phase of the first step, during which the electronic system applies to the measured quantity of thermoplastic, via the stepping-control motor (7), a force equal to that which has to be applied during the rheological measurement to be carried out.

8. Apparatus according to claim 6, characterized in that the measurement time is 10 to 60 seconds, the apparatus carrying out at least three successive measurements of equal duration during this time and carrying out a comparison between these successive measurements and their mean in order to detect a possible discrepancy in excess of 25% between these measurements and their mean.

9. Apparatus according to claim 1, equipped with a suitable die (6) for the measurement of a viscosity and/or a swelling, characterized in that after 5 to 30 seconds of thermal conditioning of the measured quantity of thermoplastic to be evaluated, the electronic system determines, as a function of the position of the plunger (3) in contact with the measured quantity and of the time of thermal conditioning, the mean speed at which the plunger (3) must travel to bring the latter to the predetermined distance from the die (6) at the end of the period of time assigned to the thermal conditioning, and compares this average speed to the constant speed to be imposed on the plunger (3) for the measurement to be carried out, and then, in a first step, monitors the stepping-control motor (7) so that the plunger (3) travels at a higher or lower speed than this average speed and, in a second step, monitors the stepping-control motor (7) so that the plunger (3) travels at the constant speed specified for the measurement to be carried out, this second step being initiated at an instant such that this constant speed of travel of the plunger (3) brings the latter to the predetermined distance from the die (6) at the end of the time period assigned to the thermal conditioning, this constant speed of travel of the plunger being maintained for the entire duration of the measurement to be carried out.

10. Apparatus according to claim 9, characterized in that said apparatus comprises means for carrying out a plurality of successive measurement of the force applied to the plunger (3) during the 30 seconds preceding the moment when the plunger (3) reaches the predetermined distance from the die, and for comparing these measurements with each other and with their mean so as to detect any discrepancy in excess of 5%.

11. Apparatus as defined in claim 1 characterized in that said electronic microprocessor system monitors the stepping-control motor (7) as a function of the position of the plunger (3).

12. Apparatus as defined in claim 1 characterized in that said electronic microprocessor system monitors the stepping-control motor (7) as a function of the signal emitted by the force-sensor.

* * * * *